United States Patent [19]
Baxter et al.

[11] Patent Number: 6,048,841
[45] Date of Patent: Apr. 11, 2000

[54] PEPTIDYL COMPOUNDS

[75] Inventors: Andrew Douglas Baxter; John Gary Montana, both of Cambridge, United Kingdom

[73] Assignee: Darwin Discovery, Ltd., United Kingdom

[21] Appl. No.: 08/755,071

[22] Filed: Nov. 22, 1996

[30] Foreign Application Priority Data

Nov. 22, 1995 [GB] United Kingdom .................. 9523828
Apr. 4, 1996 [GB] United Kingdom .................. 9607121

[51] Int. Cl.⁷ .............................. A61K 38/00; C07K 5/00
[52] U.S. Cl. ........................ 514/18; 514/19; 514/235.8; 530/331; 530/868
[58] Field of Search ............................. 514/18.19, 235.8; 530/331, 868

[56] References Cited

U.S. PATENT DOCUMENTS 5,525,629 6/1996 Crimmin et al. ..................... 514/542
5,853,623 12/1998 Montana et al. ..................... 260/998.2

FOREIGN PATENT DOCUMENTS

| 2268934 | 1/1994 | United Kingdom . |
| 9513289 | 5/1995 | WIPO . |
| 9523790 | 9/1995 | WIPO . |
| 9611209 | 4/1996 | WIPO . |

OTHER PUBLICATIONS

Fournie—Zalvski et al., Eur. J. Biochem. vol. 139 pp. 267–274 (1984).

*Primary Examiner*—Bennett Celsa
*Attorney, Agent, or Firm*—Saliwanchik, Lloyd & Saliwanchik

[57] ABSTRACT

Peptidyl compounds having an imidazole substituent have therapeutic utility via their inhibitory effect on metalloproteinases and tumour necrosis factor.

17 Claims, No Drawings

PEPTIDYL COMPOUNDS

FIELD OF THE INVENTION

This invention relates to a novel class of peptidyl derivatives and to their use in medicine.

BACKGROUND OF THE INVENTION

Metalloproteinases, including matrix metalloproteinase (MMP), (human fibroblast) collagenase, gelatinase and tumour necrosis factor (TNF), and their modes of action, and also inhibitors thereof and their clinical effects, are described in WO-A-9611209, the content of which is incorporated herein by reference.

Compounds which have the property of inhibiting the action of metalloproteinases involved in connective tissue breakdown such as collagenase, stromelysin and gelatinase have been shown to inhibit the release of TNF both in vitro and in vivo. See Gearing et al (1994), Nature 370:555-557; McGeehan et al (1994), Nature 370:558-561; GB-A-2268934; and WO-A-9320047. All of these reported inhibitors contain a hydroxamic acid zinc binding group, as do the imidazole-substituted compounds disclosed in WO-A-9523790. Other compounds that inhibit MMP and TNF are described in WO-A-9513289 and WO-A-9611209.

Compounds that inhibit collagenase, which possess structural portions akin to those of the instant invention, include those encompassed by U.S. Pat. No. 4,511,504 issued Apr. 16, 1985; and U.S. Pat. No. 4,568,666, issued Feb 4, 1986.

Compounds of related structure that are claimed to inhibit stromelysin (proteoglycanase) are encompassed by U.S. Pat. No. 4,771,037, issued Sep. 13, 1988.

Recent reports suggest that new enzymes of the MMP family also mediate the shedding of adhesion molecules such as the selecting, such as L-selectin. These soluble adhesion molecules are implicated in a number of diseases including cancer, autoimmunity and in the inflammatory response. It has been proposed that, once cleaved, the selectin bind to particular ligands and this accounts for their biological activity. Thus, drugs that interfere with or prevent binding of the ligands to the selectins will be useful medicaments for treating a variety of the diseases described above.

SUMMARY OF THE INVENTION

The invention encompasses novel mercaptoalkylpeptidyl compounds of formula (I) which are useful inhibitors of matrix metalloproteinases and/or TNFα-mediated diseases including degenerative diseases and certain cancers.

A novel compound according to the invention is of general formula (I):

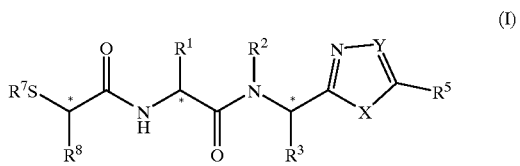

wherein:

$R^1$ is a $C_{1-6}$ alkyl, $C_{2-6}$ alkenyl, ($C_{1-6}$ alkyl)aryl, aryl, $C_{1-6}$ alkylheteroaryl, heteroaryl or $C_{1-6}$ alkyl-$AR^9$ group where A is O, $NR^9$ or $S(O)_m$ where m=0–2, and $R^9$ is H, $C_{1-4}$ alkyl, aryl, heteroaryl, ($C_{1-4}$ alkyl)aryl or ($C_{1-4}$ alkyl) heteroaryl; if $A=NR^9$ the groups $R^9$ may be the same or different;

$R^2$ is hydrogen or a $C_{1-6}$ alkyl group;

$R^3$ is a $[Alk]_n R^6$ group where Alk is a $C_{1-6}$ alkyl or $C_{2-6}$ alkenyl group and n is zero or 1;

X is $NR^9$, O or S;

Y is N or $CR^4$;

$R^4$ and $R^5$ are the same or different and are $R^9$, $COR^{13}$, $C_{1-3}$ alkyl-$R^{13}$ or $C_{1-3}$ alkyl-$COR^{13}$;

$R^7$ is hydrogen or $R^{10}CO$ where $R^{10}$ is $C_{1-4}$ alkyl, $C_{1-4}$ alkylaryl, $C_{1-4}$ alkylheteroaryl, cyclo($C_{3-6}$)alkyl, $C_{1-4}$ alkyl-cyclo($C_{3-6}$)alkyl, $C_{2-6}$ alkenyl, $C_{2-6}$ alkenylaryl, aryl or heteroaryl;

$R^8$ is aryl (optionally substituted with $R^{11}$), heteroaryl (optionally substituted with $R^{11}$), $C_{1-4}$ alkyl (optionally substituted with $R^{11}$), $C_{1-4}$ alkylaryl (optionally substituted with $R^{11}$), $C_{1-4}$ alkylheteroaryl (optionally substituted with $R^{11}$), cyclo($C_{3-6}$) alkyl (optionally substituted with $R^{11}$), cyclo($C_{3-6}$)alkenyl (optionally substituted with $R^{11}$) or $C_{1-4}$ alkyl-cyclo($C_{3-6}$)alkyl (optionally substituted with $R^{11}$), the group

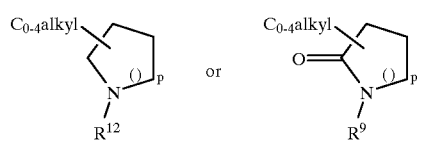

where p=1–2, or the group

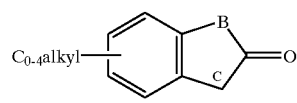

where B and C are independently selected from O, S, $C(R^9)_2$ and $NR^9$;

$R^6$ is $AR^9$, cyclo($C_{3-6}$)alkyl, cyclo($C_{3-6}$)alkenyl, $C_{1-6}$ alkyl, $C_{1-6}$ alkoxyaryl, benzyloxyaryl, aryl, heteroaryl, $C_{1-3}$ alkylheteroaryl, $C_{1-3}$ alkylaryl, $C_{1-6}$ alkyl-$COOR^9$, amidine, guanidine, $C_{1-6}$ alkyl-$NHR^{10}$, $CONHR^{10}$, $NHCO_2R^{10}$, $NHSO_2R^{10}$ or $NHCOR^{10}$;

$R^{11}$ is $SO_2R^{13}$, $SR^7$, $CO_2R^9$, $COR^9$, $CON(R^9)_2$ (where the $R^9$'s are the same or different), $N(R^9)_2$ (where the $R^9$'s are the same or different), $NR^9R^{12}$, $OR^9$, phthalimido or succinimido;

$R^{12}$ is hydrogen or a $COR^9$, $CO_2R$ (where $R^9$ is not H), $CONHR^9$, or $SO_2R^9$ (where $R^9$ is not H) group; and $R^{13}$ is a $N(R^9)_2$ (in which the $R^9$'s are the same or different), $C_{1-4}$ alkyl, aryl, heteroaryl, $C_{1-4}$ alkylaryl or cam$_{1-4}$ alkylheteroaryl;

and the salts, solvates and hydrates thereof.

DESCRIPTION OF THE INVENTION

It will be appreciated that the compounds according to the invention can contain one or more asymmetrically substituted carbon atoms, for example those marked with an asterisk in formula (I). The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

In the formulae herein, the—line is used at a potential asymmetric centre to represent the possibility of R- and S-configurations, the <line and the . . . line to represent a unique configuration at an asymmetric centre.

As used in this specification, alone or in combination, the term "$C_{1-6}$ alkyl" refers to a straight or branched chain alkyl moiety having from one to six carbon atoms, including for example, methyl, ethyl, propyl, isopropyl, butyl, tert-butyl, pentyl, hexyl and the like.

The term "$C_{1-4}$ alkyl" refers to a straight or branched chain alkyl moiety having from one to four carbon atoms, including for example, methyl, ethyl, propyl, isopropyl, butyl, tert-butyl and the like.

The term "$C_{2-6}$ alkenyl" refers to a straight or branched chain alkyl moiety having two to six carbon atoms and having in addition one double bond, of either E or Z stereochemistry where applicable. This term includes for example, vinyl, 1-propenyl, 1- and 2- butenyl, 2- methyl-2-propenyl etc.

The term "cyclo ($C_{3-6}$) alkyl" refers to a saturated alicyclic moiety having from three to six carbon atoms and includes for example cyclopropyl, cyclobutyl, cyclopentyl, cyclohexyl and the like.

The term "cyclo ($C_{3-6}$) alkenyl" refers to an alicyclic moiety having from three to six carbon atoms and having in addition one double bond. This term includes for example cyclopentenenyl or cyclohexenyl.

There term "aryl" means an optionally substituted phenyl or naphthyl group with the substituent(s) being selected, for example, from halogen, trifluoromethyl, $C_{1-6}$ alkyl, alkoxy, phenyl and the like.

The term "halogen" means fluorine, chlorine, bromine or iodine.

The term "heteroaryl" refers to aromatic ring systems of five to ten atoms or which at least one atom is selected from the group, O, N, or S and includes for example furanyl, thiophenyl, pyridyl, indolyl, quinolyl and the like.

The terms "protected amino" and "protected carboxy" mean amino and carboxy groups which are protected in a manner familiar to those skilled in the art. For example, an amino group can be protected by a benzyloxycarbonyl, tert-butoxycarbonyl, acetyl or like groups, or in the form of a phthalimido or like group. A carboxyl group can be protected in the form of a readily cleavable ester such as the methyl, ethyl, benzyl or tert-butyl ester.

The term "alkoxy" refers to a straight chain or branched chain alkoxy group containing a maximum of six carbon atoms, such as methoxy, ethoxy, propoxy, isopropoxy, butoxy, tert-butoxy and the like.

The term "$C_{0-4}$ alkyl" refers to a straight or branched chain alkyl moiety having from zero to four carbon atoms, including for example, methyl, ethyl, propyl, isopropyl and the like.

Salts of compounds of formula (I) include pharmaceutically-acceptable salts, for example acid addition salts derived from inorganic or organic acids, such as hydrochlorides, hydrobromides, p-toluene-sulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically labile ester of formula $CO_2Z$ where Z may be an ethyl, benzyl, phenethyl, phenylpropyl, a- or b-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl,2,4,6-trmethylbenzyloxymethyl or pivaloyloxymethyl group.

Compounds of the general formula (I) may be prepared by any suitable method known in the art and/or by the following processes It will be appreciated that where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$, $R^{12}$, $R^{13}$, A, B, C, X, Y and Z are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see "Protective Groups in Organic Synthesis", Wiley Interscience, T W Greene, PGM Wuts.

A process for preparing compounds of general formula (I) comprises of deprotecting (for example by hydrolysis) a compound of general formula (II)

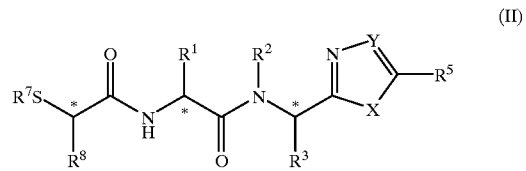

(II)

wherein $R^7$ represents a suitable protecting group (e.g. tert-butyl, trityl, benzoyl or acetate).

It will be appreciated that where a particular stereoisomer of formula (I) is required, this may be obtained by conventional resolution techniques such as high performance liquid chromatography. Where desired, however, appropriate homochiral starting materials may be used in the coupling reaction to yield a particular stereoisomer of formula (I). This is exemplified below.

Compounds of general formula (II) may be prepared by coupling an acid of formula (III)

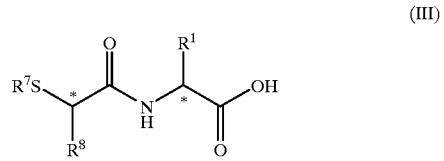

(III)

wherein $R^1$, $R^7$ and $R^8$ are as defined above, or an active derivative thereof, with an amine of formula (IV)

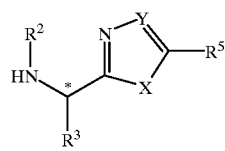

(IV)

where $R^2$, $R^3$, $R^5$, X and Y are defined previously.

Active derivatives of acids of formula (III) include for example acid anhydrides or acid halides, such as acid chlorides.

The coupling reaction may be performed using standard conditions for amination reactions of this type. Thus, the reaction may be achieved in a solvent, for example an inert organic solvent such as an ether, e.g. a cyclic ether such as tetrahydrofuran, an amide e.g. a substituted amide such as dimethylformamide, or a halogenated hydrocarbon such as dichloromethane at a low temperature e.g. $-30°$ C. to ambient temperature, such as $-20°$ C. to $0°$ C., optionally in the presence of as base, e.g. an organic base such as an amine, e.g. triethylamine or a cyclic amine such as N-methylmorpholine. Where an acid of formula (III) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate for example ethylchloroformate, prior to reaction with the amine of formula (IV).

The acid of formula (III) may be prepared by any of the processes described in WO-A-9611209.

Amines of formula (IV) may be prepared from the ketone (V) by reductive amination or reduction of the corresponding oxime (VI) which may be readily prepared from (V).

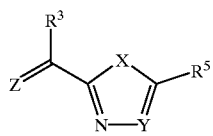

Z=O (V)
Z=NOH (VI)

Ketones of general formula (V) may be prepared from a suitably protected (e.g. with SEM) imidazole by lithiation at $-78°$ C. with n-butyllithium followed by reaction with an acid derivative of the formula $R^3$—COOH (VII). Suitable acid derivatives of formula (VII) include acid anhydrides, amides or acyl halides, such as acid chlorides.

Acids of general formula (VII) may be readily obtained from commercially-available starting materials using methods known to those skilled in the art. Some amides thereof are also commercially available.

As a further extension to the invention, heterocycles such as imidazoles, oxazoles, thiazoles and triazoles may be prepared by standard cyclisation reactions of a suitably protected aldehyde of formula $H_2N$—$CHR^3$—CHO (VIII), followed by removal of any protecting groups. For instance, imidazoles may be prepared by the reaction of a suitably protected aldehyde (VIII) with ammonia and glyoxal. Aldehydes of general formula (VIII) may be prepared by reduction of corresponding, suitably protected α-amino-acids.

Such amino-acids and their derivatives can be obtained in optically pure or racemic form. In the homochiral form they provide asymmetric building blocks for the enantiospecific synthesis of compounds of general formula (I). Many of these derivatives can be readily obtained from commercially-available starting materials using methods known to those skilled in the art. See "The Practice of Peptide Synthesis" by M. Bodanszk et al., Springer Verlag, New York (1984), and WO-A-9221360.

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol—e.g. ethanol) of a compound of formula (I) wherein $R^1$ is a $C_{2-6}$ alkenyl group. In a further example, a compound of formula (I) wherein $R^7$ is a group $R^{10}$ CO may be prepared by acylation (using a suitable acid chloride $R^{10}$ COCl, in the presence of a base such as a triethylamine in a suitable solvent, such as a chlorinated solvent—e.g. dichloromethane) of a compound of formula (I) wherein $R^7$ is H.

Any mixtures of final products or intermediates obtained can be separated on the basis of the pysico-chemical differences of the constituents, in known manner, into the pure final products or intermediates, for example by chromatography, distillation, fractional crystallisation, or by formation of a salt if appropriate or possible under the circumstances.

The compounds according to the invention exhibit in vitro inhibiting activities with respect to stromelysin, collagenase and gelatinase. Compounds according to the invention also exhibit in vitro inhibition of TNFα release. The activity and selectivity of the compounds may be determined by use of the appropriate enzyme inhibition test, for example as described in Examples A–H of WO-A-9611209. A further, fluorimetric assay is given below.

This invention also relates to a method of treatment for patients (including man and/or mammalian animals raised in the dairy, meat or fur industries or as pets) suffering from disorders or diseases which can be attributed to matrix metalloproteinases and/or TNFα as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNFA and MMPs. Accordingly in another aspect, this invention concerns:

a method of management (by which is meant treatment or prophylaxis) of disease or conditions mediated by TNFA and/or MMPs in mammals, in particular in humans, which method comprises administering to the mammal an effective, amount of a compound of formula (I) above, or a pharmaceutically-acceptable salt thereof; and a compound of formula (I) for use in human or veterinary medicine, particularly in the management (by which is meant treatment or prophylaxis) of diseases or conditions mediated by TNFA and/or MMPs; and the use of a compound of formula (I) in the preparation of an agent for the management (by which is meant treatment or prophylaxis) of diseases or conditions mediated by TNFα and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, atherosclerosis, congestive heart failure, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema and anaphylaxis.

For the treatment of rheumatoid arthritis, osteoarthritis, and in diseases and indications resulting from the overexpression of matrix metalloendoproteinases such as found in certain metastatic tumour cell lines or other diseases mediated by the matrix metalloendoproteinases or increased TNFA production, the compounds of formula (I) may be administered orally, topically, parenterally, by inhalation spray or rectally in dosage unit formulations containing non-toxic pharmaceutically-acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108;4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohos, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. (For purposes of this application, topical application shall include mouth washes and gargles).

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following non-limiting Examples are intended to illustrate the preparation of compounds of Formula (I), and as such are not intended to limit the invention as set forth in the claims appended, thereto.

In the Examples, the following abbreviations are used:

| RT | Room temperature |
|---|---|
| EDC | 1-(3-Dimethylaminopropyl)-3-ethyl carbodiimide hydrochloride |
| TNFα | Tumor necrosis factor α |
| LPS | Lipopolysaccharide |
| ELISA | Enzyme linked immunosorbent assay |

Intermediate 1 (S)—N—(Benzyloxycarbonyl)leucinal

A solution of (S)—N—(benzyloxycarbonyl)leucine methyl ester (8.22 g, 29.4 mmol) in dry toluene (80 ml) was treated dropwise at −78° C. with a solution of di-iso-butylaluminium hydride (1.0 M, 74 ml, 74 mmol) in toluene. The solution was stirred at −78° C. for 30 min. before methanol (3.5 ml) was added to quench the reaction. The cold mixture was then added to a stirred aqueous solution of potassium hydrogen tartrate (200 ml). After further stirring for 1 hour the mixture was extracted with ether (3×200 ml), the combined extracts washed with brine (400 ml), dried (MgSO$_4$) and evaporated in vacuo to provide the title compound as a colourless oil. This material was used without purification in the next step.

Similarly prepared was:

Intermediate 2 (S)—N—(Benzyloxycarbonyl) phenylalaninal

From (S)—N—(benzyloxycarbonyl)phenylalanine methyl ester (8.0 g), as a colourless oil, which was used without purification in the next step.

Intermediate 3 2-[1-(N-Benzyloxycarbonylamino)-3-methyl]butylimidazole

A solution of intermediate 1 (29.4 mmol) and glyoxal trimer dihydrate (10.36 g, 49.3 mmol) in methanol (150 ml) was treated at −15° C. with ammonia gas. After stirring for 4 hours at −10° C. the mixture was allowed to warm to RT and stirred overnight. The orange suspension was poured into water (400 ml) and the resulting white solid removed by filtration to provide the title compound (3.96 g, 47%) as a white solid.

TLC R$_f$ 0.42 (5% MeOH—CH$_2$Cl$_2$)

Similarly prepared was:

Intermediate 4 2-[1-(N-Benzyloxycarbonylamino)-2-phenyl]ethylimidazole

From intermediate 2, as an off-white solid (4.1 g, 32%).

TLC R$_f$ 0.38 (5% MeOH—CH$_2$Cl$_2$)

Intermediate 5 (S)-2-[1-(N-Benzyloxycarbonylamino)-3-methyl]-1-(1,1-dimethylethoxycarbonyl)-butylimidazole A solution of di-tert-butyldicarbonate (5.47 g, 25 mmol) in dimethylformamide (80 ml) was added dropwise to a stirred solution of intermediate 5 (7.2 g, 25 mmol), di-iso-propylethylamine (4.35 ml, 25 mmol) and dimethylaminopyridine (92 mg, 0.75 mmol) in dimethylformamide (140 ml) at 3° C. The mixture was allowed to warm slowly to RT and stirred overnight. The brown mixture was poured into water and extracted three times with ethyl acetate. The combined organic phases were washed three times with water and once with brine, dried (MgSO$_4$) and evaporated in vacuo to give the crude product as a brown oil. Purification by flash column chromatography on silica, eluting with 20% ethyl acetate-hexane, provided the desired product as a pale yellow oil. The oil was dissolved in dichloromethane (12 ml) and pentane (50 ml) was added. The mixture was placed in the freezer for 2 h after which time the precipitate was removed by filtration and the filtrate was evaporated in vacuo to give the title compound (7.70 g, 20 mmol, 79%) as a pale yellow oil.

TLC R$_f$ 0.20 (33 % ethyl acetate-hexane); ee assay 97.8%

Similarly prepared was:

Intermediate 6 (S)-2-[1-(N-Benzyloxycarbonylamino)-2-phenyl]-1-(1,1-dimethylethoxycarbonyl)-ethylimidazole From intermediate 4, as a pale yellow oil (3.52 g, 53%).

TLC R$_f$ 0.16 (33% ethyl acetate-hexane); ee assay 97.5%

Intermediate 7 (S)-2-[1-(N-Benzyloxycarbonylamino)-3-methyl]butylimidazole

Trifluoroacetic acid (15.3 ml, 198 mmol) was added to a stirred solution of intermediate 5 (7.5 g, 19.3 mmol) in dichloromethane at 3° C. The mixture was allowed to warm slowly to RT and stirred overnight. The mixture was evaporated in vacuo and then concentrated twice from a mixture of heptane and dichloromethane to give the title compound (5.53 g, 100%) as a white foam.

TLC R$_f$ 0.26 (5% methanol-dichloromethane)

Similarly prepared was:

Intermediate 8 (S)-2-[1-(N-Benzyloxycarbonylamino)-2-phenyl]ethylimidazole

From intermediate 6, as a pale yellow foam (2.5 g, 100%).

TLC R$_f$ 0.32 (5% methanol-dichloromethane)

Intermediate 9 (S)-2-(1-Amino-3-methyl)butylimidazole

A solution of intermediate 7 was hydrogenated at RT and atmospheric pressure over 10% palladium on carbon (50% w/w) in ethanol overnight. The catalyst was removed by filtration through hyflo and the filtrate evaporated to provide the crude title compound as a colourless foam, which was used directly in the next step.

Similarly prepared was:

Intermediate 10 (S)-2-(1-Amino-3-phenyl)ethylimidazole

From intermediate 8, as a pale yellow foam, which was used directly in the next step without purification.

Intermediate 11 Ethyl 5-succinimidopentanoate

Dimethylformamide (800 ml) was added to a mixture of succinimide (248 g, 2.5 mol), potassium carbonate (346 g, 2.5 mol) and ethyl 5-bromopentanoate (400 g, 1.9 mol). The mixture was heated at 110°–120° C. for 3 h before being cooled to RT. Water (2.5 L) was added and the mixture was extracted with methyl tert-butylether (4×1 L). The combined extracts were washed with water (400 ml), dried ($MgSO_4$) and evaporated in vacuo to provide the title compound (310 g, 71%) as a pale yellow oil.

TLC $R_f$ 0.3 (methyl tert-butyl ether)

Intermediate 12 5-Succinimidopentanoic acid

A solution of intermediate 11 (130 g, 572 mmol) in potassium dihydroorthophosphate (50 nM, 650 ml) was treated with Novozyme 435 (2 g). NaOH (6 N) was added in order to maintain the pH at 7. After 3 h the enzyme was removed by filtration and washed with a small amount of water. The filtrate was acidified to pH 1 by the addition of 6N hydrochloric acid, and the solution concentrated in vacuo to ca.100 ml and then extracted with dichloromethane (3×250 ml). The combined extracts were washed with brine (100 ml), dried ($MgSO_4$) and evaporated in vacuo to provide the title compound (99 g, 81%) as a white solid.

TLC $R_f$ 0.2 (50% ethyl acetate/hexane)

Intermediate 13 (R,S)-2-Bromo-5-succinimidopentanoic acid

A solution of intermediate 12 (60 g, 300 mmol) in 1,2-dichloroethane (120 ml) was treated dropwise at 80° C. with thionyl chloride (26.6 ml, 370 mmol). The mixture was stirred for 30 min before phosphorus trichloride (2.6 ml, 30 mmol) was added. Bromine (18.6 ml, 360 mmol) was then added dropwise over 20 min and the mixture stirred at 80° C. for 16 h. The mixture was cooled to RT and water (200 ml) was added; stirring was then resumed at 50° C. for 2.5 h. The mixture was cooled to RT, the precipitate collected by filtration and dried in vacuo to provide the title compound (82 g, 98%) as a pale orange powder.

TLC $R_f$ 0.3 (50% ethyl acetate/hexane)

Intermediate 14 (R, S) -2-Acetylmercapto-5-succinimidopentanoic acid

A solution of intermediate 13 (20 g, 72 mmol) in tetrahydrofuran (100 ml) was treated portionwise at 5° C. with potassium thioacetate (8.21 g, 72 mmol). The mixture allowed to warm to RT and stirred for 4 h. The solvent was evaporated in vacuo and the residue partitioned between methyl tert-butyl ether (400 ml) and water (40 ml). The organic phase was separated, washed with water (40 ml), dried ($MgSO_4$) and evaporated in vacuo to provide the title compound (14.4 g, 78%) as a yellow oil.

TLC $R_f$ 0.3 (50 % ethyl acetate/hexane)

Intermediate 15 (1S)-[(N-Benzyloxycarbonyl)-L-(S-methyl)cysteinyl]amino-3-methyl-2-butylimidazole A solution of N-benzyloxycarbonyl-L-(S-methyl) cysteine (3.50 g, 14.8 mmol) in tetrahydrofuran (60 ml) was treated at 0° C. with intermediate 9 (2.07 g, 13.5 mmol) and EDC (2.82 g, 14.8 mmol). The mixture was then allowed to warm to RT and stirred overnight. The mixture was concentrated in vacuo to ca. 30 ml and IN hydrochloric acid (20 ml) added. The mixture was then extracted with dichloromethane (5×100 ml) and the combined extracts washed with brine (100 ml), dried ($MgSO_4$) and evaporated in vacuo to provide the title compound (3.40 g, 68%) as a colourless oil.

TLC $R_f$ 0.3 (5 % MeOH—$CH_2Cl_2$)

Similarly prepared was:

Intermediate 16 (1S)-[(N-Benzyloxycarbonyl)-L-norvalinyl]amino-3-methyl-2-butylimidazole From N-benzyloxycarbonyl-L-norvaline (3.43 g, 15 mmol) and intermediate 9 (2.20 g, 14 mmol), as a pale yellow oil (94%).

TLC $R_f$ 0.4 (5% MeOH—$CH_2Cl_2$)

Intermediate 17 (1S)-[L-(S-methyl) cysteinyl]amino-3-methyl-2-butylimidazole

A solution of intermediate 15 (3.40 g, 9.2 mmol) in dichloromethane (100 ml) was treated at 0° C. with trifluoroacetic acid (11.4 ml, 14.8 mmol). The mixture was warmed to RT and stirred overnight. The solvent was evaporated in vacuo and the residue dissolved in water (50 ml). 1N NaOH was added until the solution was reached pH 8. The mixture was then extracted with dichloromethane (3×100 ml), the combined extracts washed with brine (100 ml), dried ($MgSO_4$) and evaporated in vacuo to provide the title compound (0.99 g, 40%) as a colourless oil.

TLC $R_f$ 0.1 (5 % MeOH—$CH_2Cl_2$)

Similarly prepared was:

Intermediate 18 (1S)-(L-Norvalinyl) amino-3-methyl-2-butylimidazole

From intermediate 16 (5.0 g, 14 mmol), as a white solid (50%).

TLC $R_f$ 0.2 (5 % MeOH—$CH_2Cl_2$)

Example 1 (1S)-[[(2R,S)-Acetylmercapto-5-phthalimido]-pentanoyl-L-leucyl]amino-3-methyl-2-butylimidazole A solution of (R,S)-2-acetylmercapto-5-phthalimidopentanoyl-L-leucine (Intermediate 122 of WO-A-9611209; 1 mmol) and intermediate 9 (1 mmol) in dry tetrahydrofuran (30 ml) was treated with N-hydroxybenzotriazole (1 mmol) and EDC (1 mmol) and the mixture stirred at RT overnight. The mixture was diluted with ethyl acetate (100 ml) and the solution washed with 8% sodium bicarbonate (50 ml), 1N hydrochloric acid (50 ml), water (50 ml) and brine (50 ml), dried ($MgSO_4$) and evaporated in vacuo to a pale yellow foam. Purification by flash column chromatography on silica, eluting with 2–3% methanol-dichloromethane, provided the title compound (43%) as a colourless foam.

$C_{29}H_{39}N_5O_5S$ [569.7]; $MH^+$ 570

Similarly prepared were:

Example 2 (1S)-[[(2S)-Acetylmercapto-5-phthalimido]-pentanoyl-L-(S-methyl)cysteinyl]amino-3-methyl-2-butylimidazole From (S)-2-acetylmercapto-5-phthalimidopentanoyl-L-(S-methyl)cysteine (WO-A-9611209) and intermediate 9 (0.65 mmol), as a colourless foam (46%).

$C_{27}H_{35}N_5O_5S_2$ [573.7]; MH+574

Example 3 (1S)-[[(2S)-Acetylmercapto-5-phthalimido]-pentanoyl-L-(S-methyl)cysteinyl]amino-2-phenyl-2-butylimidazole From intermediate 2 and intermediate 12 (0.65 mmol), as a colourless foam (46%).

$C_{30}H_{33}N_5O_5S_2$ [607.8]; $MH^+$ 608

Example 4 (1S) -[[(2S)-Acetylmercapto-5-succinimido]-pentanoyl-L-(S-methyl)cysteinyl]amino-3-methyl-2-butylimidazole A solution of intermediate 17 (1.61 g, 5.96 mmol) in tetrahydrofuran (32 ml) was treated at RT with intermediate 14 (1.62 g, 5.96 mmol) and EDC (1.25 g, 6.55 mmol). The mixture was then stirred overnight. The mixture was partitioned between ethyl acetate (100 ml) and water (75 ml) and the organic phase was separated, washed with brine (50 ml), dried ($MgSO_4$) and evaporated in vacuo to provide 35 a yellow oil. Purification by flash column chromatography on silica, eluting with 60% ethyl acetate-hexane, provided the title compound (1.60 g, 51%) as a white foam.
TLC R$_f$ 0.3 (5 % MeOH-CH$_2$Cl$_2$)
Similarly prepared was:
Example 5 (1S)-[[(2S)-Acetylmercapto-5-succinimido]-pentanoyl-L-norvalinyl]amino-3-methyl-2-butylimidazole
From intermediate 18 (1.76 g, 6.98 mmol) and intermediate 14 (1.90 g, 6.98 mmol), as a white solid oil (45%).
TLC R$_f$ 0.3 (5 % MeOH-CH$_2$Cl$_2$)
Example 6 (1S)-[[(2R,S)-Mercapto-5-phthalimido]-pentanoyl-L-leucyl]amino-3-methyl-2-butylimidazole
An aqueous solution of ammonia (SG 0.88, 0.3 ml) was added to a solution of Example 1 (120 mg, 0.21 mmol) in methanol at 3° C. After 1 hour the mixture was concentrated in vacuo to provide the crude product. Purification by column chromatography, eluting with 2–3% methanol in dichloromethane, furnished the title compound (76 mg, 68%) as a white solid.
C$_{27}$H$_{33}$N$_5$O$_4$S (515.7); MH$^+$516
Similarly prepared were:
Example 7 (1S)-[[(2S)-Mercapto-5-phthalimido]-pentanoyl-L-(S-methyl)cysteinyl]amino-3-methyl-2-butylimidazole
From Example 2 (4.4 g, 7.67 mmol). Purification of the crude product by column chromatography, eluting with 2–3% methanol in dichloromethane, furnished the title compound (3.0 g, 74%) as a white solid. C$_{25}$H$_{33}$N$_5$O$_4$S$_2$ [531.7]; MH$^+$ 532
Example 8 (1S)-[[(2S)-Mercapto-5-phthalimido]-pentanoyl-L-leucyl]amino-3-methyl-2-butylimidazole
From Example 3 (200 mg, 0.33 mmol). Purification of the crude product by column chromatography, eluting with 2% methanol in dichloromethane, furnished the title compound (148 mg, 79%) as a white solid.
C$_{28}$H$_{31}$N$_5$O$_4$S$_2$ [565.7]; MH$^+$ 566
Example 9 (1S)-[[(2S)-Mercapto-5-phthalimido]-pentanoyl-L-(S-methyl)cysteinyllamino-2-phenyl-2-butylimidazole
From Example 3, as a white solid oil (89%).
TLC R$_f$ 0.2 (5% MeOH—CH$_2$Cl$_2$)
Example 10 (1S)-[[(2S)-Mercapto-5-phthalimido]-pentanoyl-L-leucyl]amino-3-methyl-2-butylimidazole hydrochloride
A solution of hydrochloric acid in ether (1.0 M, 5 ml) was added to a stirred solution of Example 7 (40 mg) in a mixture of tetrahydrofuran (4 ml) and methanol (1 ml). After 1 hour at RT the mixture was concentrated in vacuo to provide the hydrochloride salt as a pale yellow solid.

MMP Inhibition Activity-Fluorimetric Assay

The potency of compounds of general formula (I) to act as inhibitors of collagenase-1 (MMP-1), collagenase-2 (MMP-8), gelatinase-A (MMP-2), gelatinase-B (MMP-9) and stromelysin-1 (MMP-3) may be determined using the following procedure:

Inhibitors are dissolved in dimethylsulphoxide containing 0.02% β-mercaptoethanol and serial dilutions are prepared. Activated enzyme is incubated in assay buffer containing 50 mM Tris, pH 7.4, 5 mM CaCl$_2$, 0.002% NaN$_3$ and Brij 35 in the presence and absence of inhibitor. Samples are pre-incubated at 37° C. for 15 minutes before the addition of the fluorimetric substrate (Mca—Pro—Leu—Dpa—Ala—Arg—NH$_2$) to a final concentration of 10 µM. The assay is incubated for 90 minutes at 37° C. and then read in a Fluoroscan II at λ$_{ex}$ (355 nm) and λ$_{em}$ (460 nm).

The enzyme activity is compared to activity in a control devoid of inhibitor and the results reported as that inhibitor concentration effecting 50% inhibition of the stromelysin (IC$_{50}$).

We claim:
1. Compounds of general formula (I):

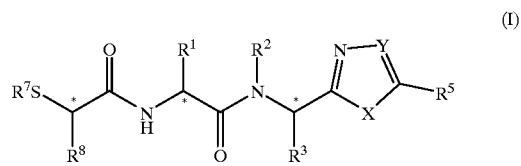

wherein:

R$^1$ is a C$_{1-6}$ alkyl, C$_{2-6}$ alkenyl, (C$_{1-6}$ alkyl)aryl, aryl, C$_{1-6}$ alkylheteroaryl, heteroaryl or C$_{1-6}$ alkyl-AR$^9$ group where A is O, NR$^9$ or S(O)$_m$ where m=0–2, and R$^9$ is H, C$_{1-4}$ alkyl, aryl, heteroaryl, (C$_{1-4}$ alkyl)aryl or (C$_{1-4}$ alkyl)heteroaryl; if A=NR$^9$ the groups R$^9$ may be the same or different;

R$^2$ is hydrogen or a C$_{1-6}$ alkyl group;

R$^3$ is a [Alk]$_n$R$^6$ group where Alk is a C$_{1-6}$ alkyl or C$_{2-6}$ alkenyl group and n is zero or 1;

X is NR$^9$, O or S

Y is N or CR$^4$;

R$^4$ and R$^5$ are the same or different and are each R$^9$, COR$^{13}$, C$_{13}$ alkyl-R$^{13}$ or C$_{1-3}$ alkylCOR$^{13}$;

R$^7$ is hydrogen or R$^{10}$CO where R$^{10}$ is C$_{1-4}$ alkyl, C$_{1-4}$ alkylaryl, C$_{1-4}$ alkylheteroaryl, cyclo(C$_{3-6}$)alkyl, C$_{1-4}$ alkyl-cyclo(C$_{3-6}$)alkyl, C$_{2-6}$ alkenyl, C$_{2-6}$ alkenylaryl, aryl or heteroaryl;

R$^8$ is aryl (optionally substituted with R$^{11}$), heteroaryl (optionally substituted with R$^{11}$), C$_{1-4}$ alkyl (optionally substituted with R$^{11}$), C$_{1-4}$ alkylaryl (optionally substituted with R$^{11}$), C$_{1-4}$ alkylheteroaryl (optionally substituted with R$^{11}$), cyclo (C$_{3-6}$) alkyl (optionally substituted with R$^{11}$), cyclo(C$_{3-6}$)alkenyl (optionally substituted with R$^{11}$) or C$_{1-4}$ alkyl-cyclo(C$_{3-6}$)alkyl (optionally substituted with R$^{11}$), the group

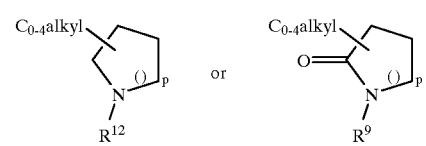

where p=1–2, or the group

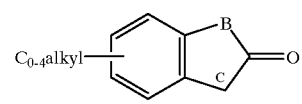

where B and C are independently selected from the group O, S, C(R$^9$)$_2$ and NR$^9$, and the R$^9$'s are the same or different;

R$^6$ is AR$^9$, cyclo(C$_{3-6}$)alkyl, cyclo(C$_{3-6}$)alkenyl, C$_{1-6}$ alkyl, C$_{1-6}$ alkoxyaryl, benzyloxyaryl, aryl, heteroaryl, C$_{1-3}$ alkylheteroaryl, C$_{1-3}$ alkylaryl, C$_{1-6}$ alkyl-COOR$^9$, amidine, guanidine, C$_{1-6}$ alkyl-NHR$^{10}$, CONHR$^{10}$, NHCO$_2$R$^{10}$, NHSO$_2$R$^{10}$ or NHCOR$^{10}$;

R$^{11}$ is SO$_2$R$^{13}$, SR$^7$, CO$_2$R$^9$, COR$^9$, CON(R$^9$)$_2$ (where the R$^9$'s are the same or different), N(R)$_2$ (where the R$^9$'s are the same or different), NR$^9$R$^2$, OR$^9$, phthalimido or succinimido;

R$^{12}$ is hydrogen or a COR$^9$, CO$_2$R$^9$ (where R$^9$ is not H), CONHR$^9$, or SO$_2$R (where R is not H) group; and $R^{13}$ is a $N(R^9)_2$ (in which the $R^9$'s are the same or different), $C_{1-4}$ alkyl, aryl, heteroaryl, $C_{1-4}$ alkylaryl or $C_{1-4}$ alkylheteroaryl;

and the salts, solvates and hydrates thereof.

2. The compound of claim 1, wherein $R^6$ is not amidine or guanidine; $R^8$ is substituted if it is aryl, alkyl or alkylaryl; and $R^{11}$ is $SO_2R^{13}$, $SR^7$, $COR^{13}$, $N(R^9)_2$, $NR^9R^{12}$, $OR^9$, phthalimido or succinimido.

3. The compound of claim 1, selected from the group consisting of (1S)-[[(2R,S)-Acetylmercapto-5-phthalimido]pentanoyl-L-leucyl]amino-3-methyl-2-butylimidazole and (1S)- [(2S)-Acetylmercapto-5-phthalimido]pentanoyl-L-(S-methyl)cysteinyl]amino-3-methyl-2-butylimidazole.

4. The compound of claim 1, selected from the group consisting of (1S)-[[(2S)-Acetylmercapto-5-phthalimido]pentanoyl-L-(S-methyl)cysteinyl]amino-2-phenyl-2-butylimidazole;

(1S)-[[(2R,S)-Mercapto-5-phthalimido]pentanoyl-L-leucyl]amino-3-methyl-2-butylimidazole;

(1S)-[[(2S)-Mercapto-5-phthalimido]pentanoyl-L-(S-methyl)cysteinyl]amino-3-methyl-2-butylimidazole; and (1S)-[[(2S)-Mercapto-5-phthalimido]pentanoyl-L-leucyl]amino-3-methyl-2-butylimidazole and its hydrochloride.

5. The compound of claim 1, selected from the group consisting of (1S)-[[(2S)-Acetylmercapto-5-succinimido]-pentanoyl-L-(S-methyl)cysteinyl]amino-3-methyl-2-butylimidazole;

(1S)-[[(2S)-Acetylmercapto-5-succinimido]-pentanoyl-L-norvalinyl]amino-3-methyl-2-butylimidazole; and (1S)-[[(2S)-Mercapto-5-phthalimido]-pentanoyl-L-(S-methyl)cysteinyl]amino-2-phenyl-2-butylimidazole.

6. The compound of claim 1, in the form of a single enantiomer or diastereomer, or a mixture of such isomers.

7. The compound of claim 1, wherein $R^8$ is $C_{1-4}$ alkyl substituted with $R^{11}$.

8. A pharmaceutical composition comprising a compound of claim 1, and a pharmaceutically-acceptable diluent, or carrier.

9. A method for the treatment in a human or an aninal of a condition associated with matrix metalloproteiiases or that is mediated by TNFα or L-selectin sheddase, wherein said method comprises administration of an effective amount of a compound of claim 1 to said human or animal.

10. The method according to claim 9, wherein the condition is selected from the group consisting of cancer, inflammation and inflammatory diseases, tissue degeneration, periodontal disease, ophthalmological disease, dermatological disorders, fever, cardiovascular effects, haemorrhage, coagulation and acute phase response, cachexia and anorexia, acute infection, HIV infection, shock states, graft versus host reactions, autoimmune disease, reperfusion injury, meningitis, and migraine.

11. The methods according to claim 9, wherein the condition is selected from the group consisting of tumour growth, angiogenesis, tumour invasion and spread, metastases, malignant ascites and malignant pleural effusion.

12. The methods according to claim 9, wherein the condition is selected from the group consisting of rheumatoid arthritis, osteoarthritis, osteoporosis, asthma, multiple sclerosis, neurodegeneration, Alzheimer's disease, atherosclerosis, stroke, vasculitis, Crohn's disease and ulcerative colitis.

13. The method according to claim 9, wherein the condition is selected from the group consisting of corneal ulceration, retinopathy and surgical wound healing.

14. The method according to claim 9, wherein the condition is selected from the group consisting of psoriasis, atopic dermatitis, chronic ulcers and epidermolysis bullosa.

15. The method according to claim 9, wherein the condition is selected from the group consisting of periodontitis and gingivitis.

16. The method according to claim 9, wherein the condition is selected from the group consisting of rhinitis, allergic conjunctivitis, eczema and anaphalaxis.

17. The method according to claim 9, wherein the condition is selected from the group consisting of ristonosis, congestive heart failure, endometriosis, atherosclerosis and endosclerosis.

* * * * *

UNITED STATES PATENT AND TRADEMARK OFFICE
CERTIFICATE OF CORRECTION

PATENT NO.  : 6,048,841
DATED       : April 11, 2000
INVENTOR(S) : Andrew Douglass Baxter, John Gary Montana It is certified that error appears in the above-identified patent and that said Letters Patent is hereby corrected as shown below:

Column 14,
Line 23: "O or S" should read --O or S;--.
Line 26: "$C_{13}$ alkyl-$R^{13}$" should read --$C_{1-3}$alkyl-$R^{13}$--.
Line 29: "alkyl-cyclo" should read --alkylcyclo--.
Line 64: "$NR^9R^2$" should read --$NR^9R^{12}$--.
Line 67: "(where R is not H)" should read --(where $R^9$ is not H)--.

Column 15,
Line 13: "(1S)- [(2S)-Acetylmercapto" should read --(1S)- [[(2S)-Acetylmercapto--.

Column 16,
Line 1: "aninal" should read --animal--.
Line 2: "metalloproteiiases" should read --metalloproteinases--.
Line 16: "The methods" should read --The method--.
Line 22: "The methods" should read --The method--.
Line 42: "ristonosis" should read --restenosis--.

Signed and Sealed this

Nineteenth Day of June, 2001

*Attest:*

*Attesting Officer*

NICHOLAS P. GODICI
*Acting Director of the United States Patent and Trademark Office*